United States Patent [19]

Kesling

[11] Patent Number: 5,098,288

[45] Date of Patent: Mar. 24, 1992

[54] FLEXIBLE BONDING PAD FOR AN ORTHODONTIC BRACKET

[75] Inventor: Peter C. Kesling, LaPorte, Ind.

[73] Assignee: TP Orthodontics, Inc., Westville, Ind.

[21] Appl. No.: 518,984

[22] Filed: May 4, 1990

[51] Int. Cl.$^5$ .............................. A61C 3/00
[52] U.S. Cl. .............................................. 433/9
[58] Field of Search ..................... 433/3, 4, 9, 24

[56] References Cited

U.S. PATENT DOCUMENTS

| | | |
|---|---|---|
| 3,250,003 | 5/1966 | Collito .................... 433/9 |
| 4,186,488 | 2/1980 | Wallshein ................ 433/8 |
| 4,243,386 | 1/1981 | Kawaguchi ............. 433/9 |
| 4,639,218 | 1/1987 | Jones et al. ............. 433/8 |
| 4,902,224 | 2/1990 | Collins et al. ........... 433/8 |
| 4,907,965 | 3/1990 | Martin .................... 433/3 |

OTHER PUBLICATIONS

Journal of Clinical Orthodontics, vol. XXIV, No. 2, Feb. 1990, "Debonding Ceramic Brackets", Elliot R. Storm, D.D.S.
American Journal of Orthodontics and Dentofacial Orthopedics, vol. 97, No. 2, Feb. 1990, "Ceramic Bracket Bonding: A Comparison of Bond Strength with Polyacrylic Acid and Phosphoric Acid Enamel Conditioning", A. J. Maskeroni, D.D.S. et al.

Primary Examiner—John J. Wilson
Assistant Examiner—Jeffrey A. Smith
Attorney, Agent, or Firm—Lloyd L. Zickert

[57] ABSTRACT

A relatively flexible bonding pad or base for an orthodontic bracket to facilitate debonding the bracket from a tooth and a method of debonding wherein the base or pad is secured to the bracket and the base or pad is bonded to a surface of a tooth. The base or pad is of a relatively flexible material and is formed so that it can be engaged by a pliers for the application of a compressive or buckling force to cause the base or pad to buckle or distort and break the bond to the tooth without the application of any force to the bracket which would cause fracturing of the bracket. The method would include the adhesive attachment of a plastic base or pad to a bracket prior to adhesively bonding the bracket to the tooth, and thereafter debonding by applying a force to the pad that would cause buckling and breaking of the bond with the tooth.

8 Claims, 3 Drawing Sheets

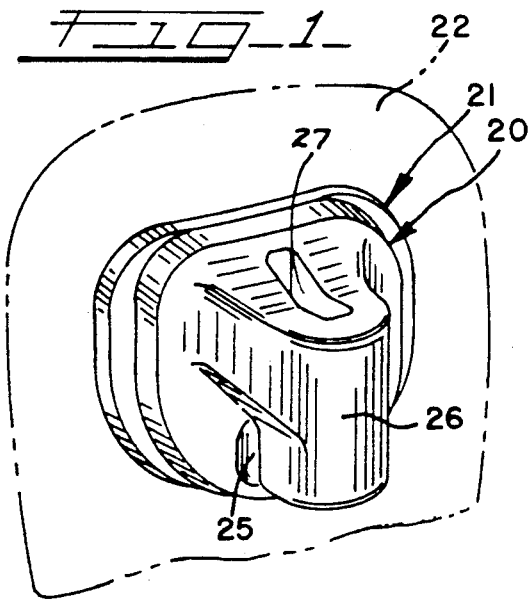
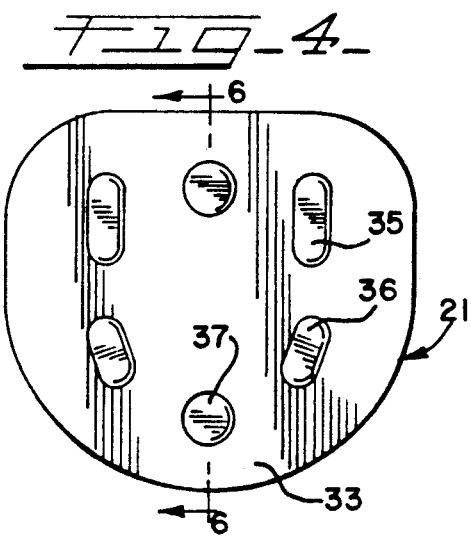
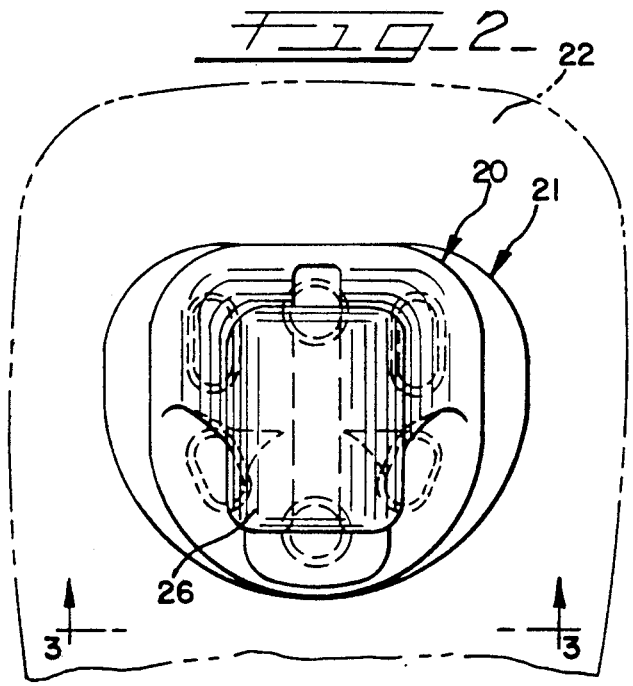
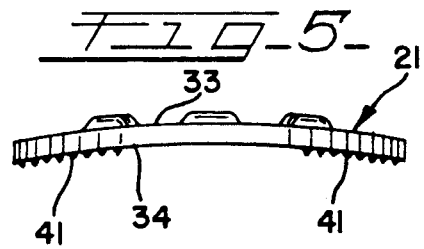
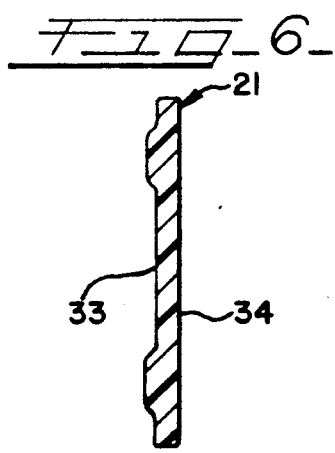
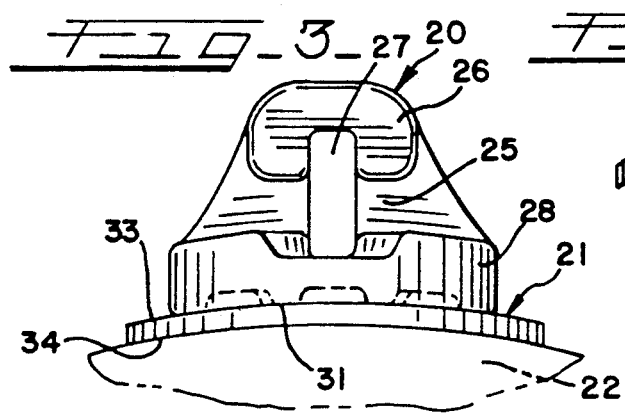
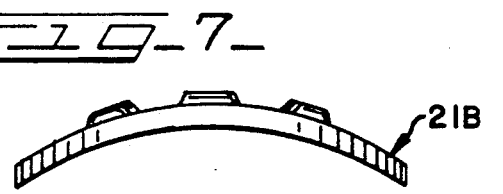
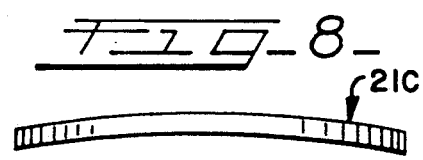

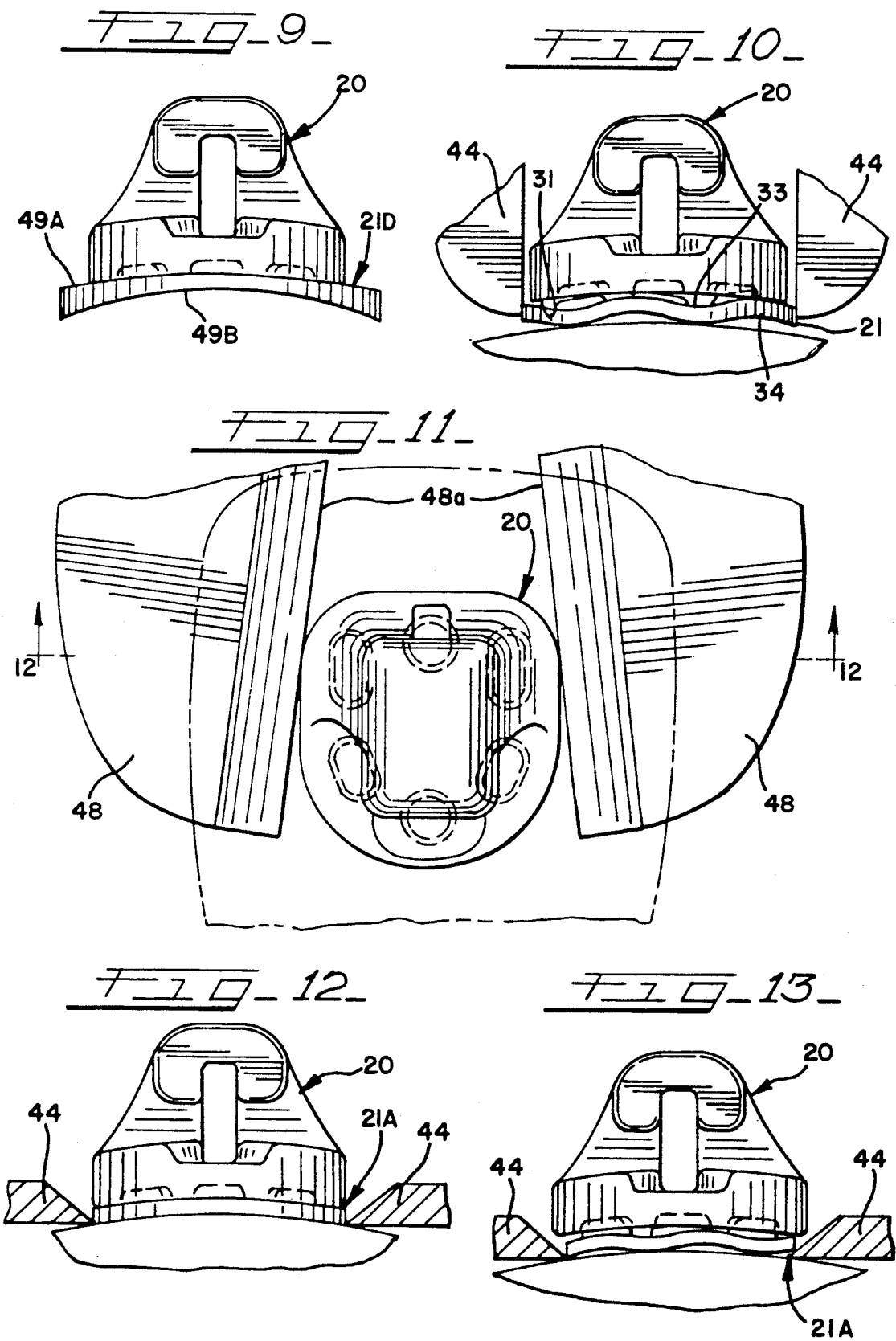

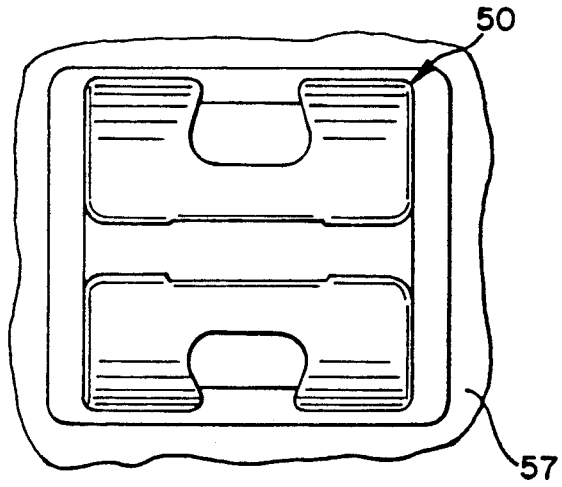
FIG_14_
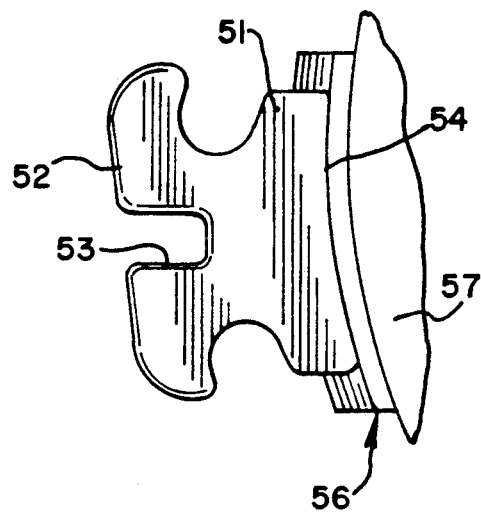
FIG_15_
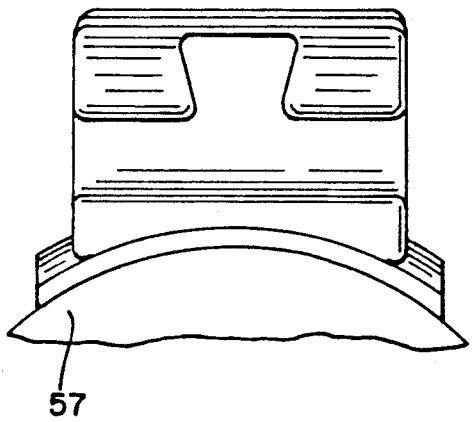
FIG_16_
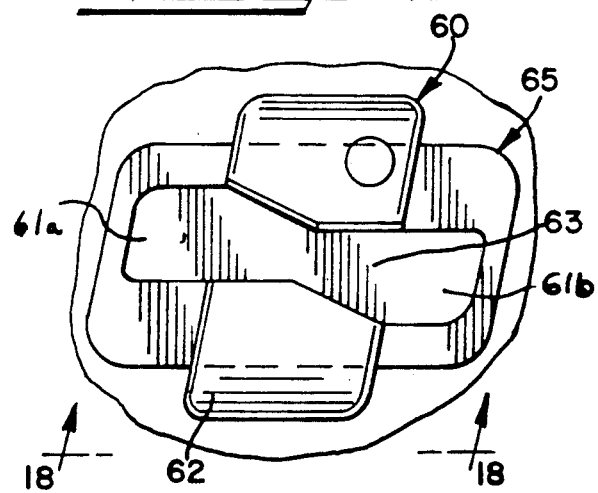
FIG_17_
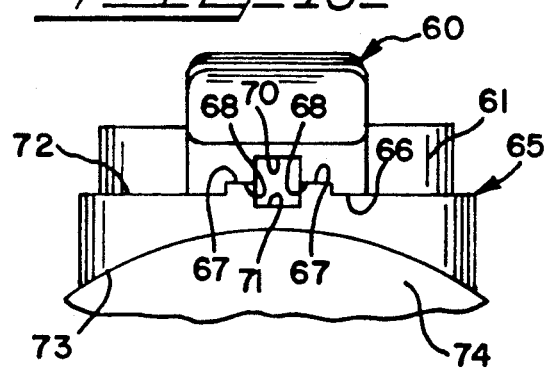
FIG_18_

FLEXIBLE BONDING PAD FOR AN ORTHODONTIC BRACKET

DESCRIPTION

This invention relates in general to a plastic pad or base for use with orthodontic brackets to permit debonding without fracturing of the bracket or damaging the tooth enamel, and more particularly to a plastic pad or base for a ceramic bracket sized to be engaged by a pliers during a debonding procedure.

BACKGROUND OF THE INVENTION

Prior to the advent of ceramic brackets, it has been known to provide metal brackets with bonding pads for direct bonding the brackets to teeth. The bonding pads are also of metal and are suitably secured to the brackets. Removal has been accomplished by the use of a standard dental pliers and can be accomplished with respect to all of the brackets in a matter of minutes.

Ceramic brackets made of monocrystalline or polycrystalline material have posed a different problem when they are bonded to teeth, as it is difficult to debond the brackets following their use.

Bonding materials of various types have been used, some of which greater bonding strength than others. These bonding materials are made and sold by a number of orthodontic supply companies. Ceramic brackets have their bases integrally formed. Such ceramic brackets are often molded and/or machined to final shape. It is a well known problem that removal of bonded ceramic brackets has proved quite difficult and can be very hazardous. For example, when a rigid bracket is removed directly from a tooth, it may cause the bracket to fracture, leaving a part of the bracket on the tooth. The other part of the bracket might shatter in the patient's mouth, setting up a situation where pieces of the bracket which are like glass might be ingested, inhaled or otherwise damage the tissues of the mouth.

When a part of the ceramic bracket is left on the tooth, it often requires grinding to be removed, and damage can easily be done to the tooth enamel.

Also, it has been known to remove part or all of the enamel during the removal of ceramic brackets, which then is injurious to the health of the tooth.

Whenever enamel is removed or the patient injured by the removal of a ceramic bracket, a potential liability problem is created for the orthodontist.

Unlike the time needed to remove metal brackets, the time needed to remove ceramic brackets is substantially greater, which then not only requires more time of the orthodontist but makes the chair time of the patient more uncomfortable.

Ceramic brackets are known to be much more rigid than metal brackets which can flex or bend during removal. Because of the inability of ceramic brackets to flex, it can be appreciated that greater forces usually are required to remove the bracket during debonding. Whenever the bracket to adhesive interface between a ceramic bracket and the tooth enamel is too strong, there is a high potential for damage of the enamel during debonding. Several attempts have been made to solve the debonding problem associated with ceramic brackets. For example, it is proposed in U.S. Pat. No. 4,455,138 that heat to the dental bracket will assist in loosening the adhesive bonding of the bracket to the tooth so that the bracket may be more easily removed with less forces. However, it has been found that this system was not always practical as the orthodontist may prematurely pull the bracket in anticipation of the loosening of adhesive, causing great pain to the patient and also shattering of the bracket before the heat applied would loosen the adhesive. Further, the pulling force could not be directionally controlled with this system.

Another debracketing tool and method of removal is disclosed in U.S. Pat. No. 4,907,965, where the heat and debracketing force is simultaneously applied. This system does not always assure that the adhesive is sufficiently loose to allow easy removal, and likewise requires engagement of the ceramic bracket during removal.

SUMMARY OF THE INVENTION

The present invention overcomes the difficulties heretofore encountered in debonding ceramic brackets by making it unnecessary to directly engage the bracket with an instrument or apply any force to the bracket during the debonding process. The present invention is in a relatively flexible pad or base that is an integral part of, or attached to the base of, a ceramic bracket so that the bracket can be bonded to the tooth through the relatively flexible pad or base. Thereafter, on debonding, a pliers or debonding tool engages the relatively flexible pad or base to apply a distorting or buckling force to the pad or base that normally breaks the bond between the pad and the bracket and can break the bond between the pad and the tooth. This eliminates the need to apply a prying or pulling force directly to the ceramic bracket. The term "buckling" is intended to mean bending under pressure and result in curling or distorting from a normal or usual state.

The pad or base is sized so that it can be engaged and buckled under a force which does not necessitate directly applying any force to the bracket.

The pad or base may be structured to be used for any presently marketed ceramic bracket by being added to the base of the bracket or as part of the bracket structured for mating engagement with a mating surface of the ceramic portion of the bracket. It may be provided in many different forms so long as it is sized to receive forces which can cause it to buckle so as to break the bond between the pad and the tooth or the pad and the bracket and permit easy removal of the bracket without requiring the application of any force directly to the bracket. To facilitate identification of brackets for particular teeth, the pads may have different colors.

While the plastic pad or base of the invention is particularly useful for ceramic brackets, it could be used with metal brackets or hard plastic brackets. The plastic pad or base would be of softer plastic than the plastic bracket.

It is therefore an object of the present invention to provide a plastic base or pad for an orthodontic bracket to enhance debonding the bracket from a tooth.

Another object of the present invention is to provide a relatively flexible pad or base of plastic for a ceramic bracket or a bracket that is part ceramic and part plastic to permit debonding without causing the ceramic bracket or ceramic bracket portion to break.

A further object of the present invention is in the provision of a ceramic bracket with a pad or base of plastic with a tooth-attaching side to be adhesively bonded to a tooth whereby the plastic portion is sized so that it can be engaged by a pliers during a debonding operation without engagement of the ceramic portion of the bracket.

Another object of the invention is in the provision of a plastic pad or base for attachment to a ceramic bracket wherein the pad is made of a plastic that has a flexibility much greater than the bracket such that when subjected to a compressive buckling-type force, it will flex and bend along the attaching sides to break the bond with the tooth in order to permit quick and easy removal of the bracket from the tooth without causing damage to the bracket, and particularly without casing breaking of the bracket which could injure the patient, thereby reducing the time needed to debond ceramic brackets and avoiding damage to the tooth enamel.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a perspective view of a light-wire ceramic bracket mounted on a tooth and having a plastic wafer/pad interposed between the bracket and the tooth;

FIG. 2 is a front elevational view of the bracket of FIG. 1 and showing the extent of size of the pad relative to the bracket and also showing in dotted lines the indent/detent alignment structure between the pad and the bracket;

FIG. 3 is a bottom plan view of the bracket of FIGS. 1 and 2 and looking along line 3—3 and in the direction of the arrows as shown in FIG. 2;

FIG. 4 is an elevational view of the plastic wafer/pad of the invention showing the bracket-attaching side;

FIG. 5 is a top elevational view of the pad of FIG. 4;

FIG. 6 is a detailed vertical sectional view taken through the pad of FIG. 4 and substantially along line 6—6 thereof;

FIG. 7 is a top elevational view of a modified pad showing a greater curvature than the pad of FIGS. 4 to 6;

FIG. 8 is a further modified pad like the pad of FIG. 5 but different in that both sides are plain or smooth;

FIG. 9 is a view of a bracket and pad like that of FIG. 3 which differs in that the tooth attaching side of the pad has a greater curvature to mate with the surface of the tooth than the bracket-attaching side of the pad;

FIG. 10 is a view illustrating the debonding of the ceramic bracket where the bracket includes a plastic wafer/pad like that shown in FIG. 3 and where the beaks of the pliers are in engagement with the side edges of the plastic pad so as to buckle or distort the pad as shown in exaggerated form and break the adhesive bonding of the bracket with the tooth;

FIG. 11 is a front or labial view of a bracket on a tooth and having a plastic pad of the same dimension as the face of the bracket and illustrating the use of a pliers where the beaks extend generally parallel to the face of the tooth;

FIG. 12 is a gingival view of the bracket of FIG. 11 and showing how the beaks of the pliers engage the plastic pad without engaging the bracket and is taken substantially along line 12—12 of FIG. 11 and looking in the direction of the arrows;

FIG. 13 is a view similar to FIG. 12 but illustrating the compressive force applied by the beaks of the pliers and showing in exaggerated form how the pad distorts to break the bond of adhesive between the pad and the bracket;

FIG. 14 is a front elevational view of another type of bracket that can utilize the plastic wafer/pad of the invention and wherein the bracket is of the edgewise type;

FIG. 15 is a side elevational view of the bracket of FIG. 14;

FIG. 16 is a bottom plan view of the bracket of FIGS. 14 and 15;

FIG. 17 is a front elevational view of a still different type of edgewise bracket comprising a ceramic top, and a plastic bottom that serves as the pad or base of the bracket to permit efficient debonding; and FIG. 18 is an occlusal plan view of the bracket shown in FIG. 17.

DESCRIPTION OF THE INVENTION

Referring now to the drawings, and particularly to FIGS. 1 to 5, a ceramic bracket 20 is illustrated in combination with a plastic wafer/pad 31 in mounting relation on a tooth 22. The bracket 21 is of the Begg or light-wire type having a vertically opening slot 25 formed in the body 26 of the bracket. A vertically extending pin slot 27 is formed in the body of the bracket and the bracket is provided with a base 28. It will be appreciated that the archwire slot 25 is adapted to receive an archwire, while a suitable pin will be used and received in the pin slot 27 to lock the archwire in place on the bracket. On the side of the base that would face the tooth, a pad-engaging face 31 is provided to which is suitably adhesively secured the plastic pad 21. This embodiment particularly illustrates the addition of a plastic pad to the base of a bracket.

The pad 31 includes a bracket-attaching side 33 and a tooth-attaching side 34. The bracket-attaching side of the plastic pad is shown in FIG. 4 and includes a plurality of detents of which detents 35 are of one shape and being somewhat oval, detents 36 are of another shape and being somewhat oval, and detents 37 being of another shape and generally circular. The detents 35, 36 and 37 are adapted to be received in indents formed in the tooth-facing surface of the bracket and the indents and detents serve to orient or align the plastic pad with the base of the bracket. The indents in the pad-attaching face 31 of the bracket are shown in dotted lines in FIGS. 2 and 3 but unnumbered for purposes of clarity. However, it will be appreciated that the indents will be formed and sized so as to define a mating relation with the detents on the pad. If desired, the detents/indents may be polygonal in shape or of any other shape.

It may be noted that the plastic pad 21 has a slight arcuate form when viewed from above, as seen particularly in FIG. 5, but it may be appreciated that it could be flat and then bent to the shape of the tooth-attaching face of the bracket as needed when adhesively securing the pad to the bracket. Further, if the tooth-facing side of the bracket were flat, the plastic pad at least on the side to be attached to the bracket would also be flat.

The plastic pad will be of a suitable plastic material for use in the mouth and which has some flexibility so that it can be buckled or distorted relative to the bracket and the tooth surface when debonding. It also must be compatible with the bonding adhesives used so that it can be properly bonded to the base of the ceramic bracket and also properly bonded to the enamel face of the tooth. The pad may be suitable molded or it may be stamped from a sheet of plastic material. Where the surfaces are specially formed, the surface area must be molded. One suitable plastic material is a polycarbonate material, although it can be appreciated that any other suitable material may be used. Further, the plastic material may be of a thermoplastic or thermosetting type.

The shape of the wafer/pad may generally take the shape of the base of the bracket. With respect to the embodiment of FIGS. 1 to 5, the pad is illustrated as being larger than the base in two directions, although it may be larger than the base in all directions. As particularly seen in FIG. 2, the plastic pad extends from the opposite sides of the bracket base. In another embodiment as described below, the plastic pad need not extend beyond the boundaries of the base.

So, as seen particularly in FIGS. 1, 2 and 3, the plastic pad extends beyond the mesial and distal sides of the bracket base and is therefore engageable by pliers when the bracket is to be debonded. The sizing is such that a compressing force applied to the pad produces a buckling action or distortion in the pad without the beaks of the pliers applying any forces to the bracket that would cause fracture of the bracket during the debonding process. While it is not necessary that the pad extend beyond the occlusal and gingival edges of the bracket base, it can extend beyond these edges if so desired, as will be seen in the embodiment of FIGS. 14 to 16.

The thickness of the pad need only be such that it can be easily engaged by the beaks of the pliers during the debonding operation, and it is relatively thin, even through it may be thicker.

As shown in FIG. 10, debonding of the bracket 20 is accomplished by applying a compressive force to the mesial and distal edges of the pad that extend beyond the base of the bracket through plier beaks 44. The force is generally applied along the surface of the tooth. Where it can be seen that the beaks extend substantially perpendicular to the pad and following the engagement of the opposed edges of the pad and the application of a compressive or buckling force, a buckling or distortion of the pad along its width will be produced, as illustrated in exaggerated form in FIG. 10, which normally results in the breaking of the adhesive bond between the bracket-engaging side 33 of the pad 21 and the bracket without necessitating the engagement or application of any force on the ceramic bracket by the beaks of the pliers. Some debonding between the pad and the tooth could also take place. Thus, any chance of fracturing the ceramic bracket is generally eliminated. It should be appreciated that pliers could even be adjusted so that the beaks could not close to the point of engagement with the bracket. The distortion of the pad effectively causes the bracket to pop off the pad. Thereafter, the pad and adhesive on the tooth can be easily removed by a scaler. Prior to applying a compressive force to the pad, if the bonding adhesive covers the edges of the pad where the pliers beaks are to engage the pad, the adhesive may be quickly removed by a dental bur to facilitate directly applying compressive forces to the pad.

Referring now to the embodiment of FIGS. 11 to 13, it will be seen that the size of the plastic wafer/pad designated by the numeral 21A is the same general size as the base of the bracket. While not shown to be any thicker than the pad 21, it could be of greater thickness if desired. This embodiment illustrates the use of a pliers of a different type having different beaks and the application of a compressive or buckling force to the pad from a different direction than the procedure shown in FIG. 10. In this embodiment, the pliers includes knife-like beaks 48, with knife-like edges 48a that can engage the pad 21a, as seen in FIG. 12, from the opposite sides and still not engage the ceramic bracket 20. As further seen in FIG. 13, with the application of a compressive force by the pliers to the pad, the pad distorts or buckles and breaks the adhesive bond between the pad and the bracket and/or the pad and the tooth to facilitate debonding of the bracket without necessitating the application of any direct force to the bracket itself. The knife edges 48a could also engage the interface between the bracket 20 and the pad 21 or 21a to distort the pad away from the bracket to break the bond and release the bracket. The beaks may be of any suitable shape that would permit application of a compressive force generally along the surface of the tooth.

Referring now to the pad 21B shown in FIG. 7, this pad differs from the pad 21 only in that it has a greater curvature. It will be appreciated that any suitable curvature may be molded into the pad so that it will make with the tooth-facing side of a bracket and the tooth.

The pad 21C shown in FIG. 8 differs from pad 21 only in that it does not includes any detents on the bracket-attaching side or any indents or roughened surfaces on the tooth-attaching side, as indicated at 41 in FIG. 5. It will be appreciated that the surfaces of the pad may be formed according to how it may best be utilized with respect to bonding to a bracket or bonding to a tooth. While the embodiment of FIG. 8 is shown to have a slight arcuate form, it may be in a flat form if so desired.

Although the pad 21, as well as the other embodiments 21A, 21B and 21C, are shown to have a uniform thickness throughout, it will be appreciated that they may be formed with a varying thickness, depending upon the application desired. As shown in FIG. 9, the pad 21D includes an upper curvature side 49a of one curvature and a lower or tooth-engaging side which is of a greater curvature and identified as 49b, giving it a varying thickness from side to side. The pad could be formed with a flat side on the side for attachment to the bracket where all brackets could be made with a flat tooth-facing surface, and with a curvature on the tooth-attaching side of the plastic pad that may be varied to mate with the curvature of a desired tooth. Thus, the plastic pad could be made with different curvatures on the tooth-engaging side.

The embodiment of FIGS. 14 to 16 is shown to illustrate the use of the bonding pad of the invention with an edgewise bracket of the type disclosed in U.S. Pat. No. 4,799,882, and which is generally designated by the numeral 50. This bracket includes a base 51 and extending therefrom a tie wing 52 having a horizontally opening archwire slot 53. At the tooth side of the base 51, a face 54 is provided and to which is adhesively bonded the plastics wafer/pad 56 which is sized to be grater on all four sides than the dimension of the base, as particularly seen in FIG. 15. The pad is shown attached to a tooth 57, and it will function in the same manner as the pads of previous embodiments in that when it is desired to debond the bracket from the tooth, a compressive/buckling force can be applied to the pad either from opposite mesial and distal sides of opposite occlusal and gingival sides in order to buckle or distort the pad and break the bond between the pad and bracket and/or also between the pad and the tooth without causing any pressure or forces to be directly applied to the bracket.

Referring now to the embodiment of FIGS. 17 and 18, another form of edgewise-type bracket is shown and generally designated by the numeral 60. This bracket is also of ceramic and of the form that is described in U.S. Pat. No. 4,842,514. Bracket 60 includes rotation control wings 61a and 61b and a tie wing 62 extending outwardly therefrom, and a horizontally opening archwire slot 63. A plastic base 65 is attached to the tooth-facing surface 66 of the bracket, and the base 65 includes a pair of ribs 67 which mate with recesses 68 on the bracket to provide an orientation or alignment between the bracket and the base. Additionally, the bracket includes an auxiliary vertical groove 70 which aligns with a groove 71 in the pad to form a closed slot. The bracket-attaching side 72 of the pad is relatively flat other than having the ribs 67 and groove formation 71, while the tooth-engaging side 73 of the pad is arcuate to ate with the arcuate surface of tooth 74. Removal of the bracket 60 during a debonding process is similarly accomplished by providing a compressive/buckling force to the plastic base by use of pliers whereby the base is buckled to break the adhesive bond between the bracket and the pad and/or between the pad and the tooth. The brackets of FIGS. 14 to 18 are only illustrative of edgewise-type brackets, and it can be appreciated the base of the invention may be used with any edgewise-type brackets as well as any light-wire bracket. As previously mentioned, if the adhesive used to bond the pad/base to the tooth interferers with the direct application of compressive forces to the pad, the adhesive can be removed with a rotary dental bur to expose the edge(s) of the pad to readily accept the direct compressive forces.

In view of the foregoing, it is now appreciated that the present invention provides a pad or base and solves the problem of debonding of a ceramic bracket from a tooth without causing damage to the tooth enamel or fracture of the bracket, and permitting debonding of ceramic brackets to be quick and easy.

While the plastic bonding pad of the invention is particularly useful to solve the debonding problems of ceramic brackets, it could also be used with metal or plastic brackets.

It will be understood that modifications and variations may be effected without departing from the scope of the novel concepts of the present invention, but it is understood that this application is to be limited only by the scope of the appended claims.

The invention is hereby claimed as follows:

1. A plastic base/pad adapted to be adhesively secured to a ceramic bracket, said base/pad having a bracket-engaging side and a tooth-engaging side adapted to be adhesively bonded to a tooth, said base/pad being sized to extend beyond opposed sides of the bracket to be easily engageable by an instrument during debonding without the instrument applying any force to the bracket, and said base/pad being of a polycarbonate plastic that upon application of a squeezing force by the instrument will buckle or distort to break the bond between the bracket and the base/pad and/or the base/pad and the tooth.

2. The plastic base/pad of claim 1, wherein the bracket is of ceramic.

3. The combination of a ceramic orthodontic bracket having a tooth-facing side and a relatively thin and flexible plastic pad, said pad having a bracket-attaching side adhesively secured to the tooth-facing side of the bracket, and a tooth-attaching side adapted to be bonded to the surface of a tooth, the tooth-facing side of the bracket and the bracket-attaching side of the pad including means for aligning the pad to the bracket when adhesively attaching the pad to the bracket, and said pad being sized to extend beyond at least two opposed edges of the tooth-engaging side of the bracket to be engageable at the edges by means for application of a compressive force without contacting the bracket when debonding the bracket from the tooth.

4. The combination of claim 3, wherein said aligning means includes indents on one of the tooth-facing side of the bracket or the bracket-attaching side of the pad and detents on the other of the tooth-facing side or the bracket-attaching side.

5. The combination of claim 3, wherein said aligning means includes ribs on one of he tooth-facing side of the bracket or the bracket-attaching side of the pad and recesses matingly receiving the ribs on the other of the tooth-facing side or the bracket-attaching side.

6. The combination of a ceramic orthodontic bracket having a tooth face and a relatively thin and flexible plastic pad of polycarbonate material, said pad having a bracket-attaching side adhesively secured to the tooth-facing side of the bracket, and a tooth-attaching side adapted to be bonded to the surface of a tooth, said pad being sized to extend beyond at least one edge of the tooth-attaching side of the bracket to be engageable by means for application of a compressive force to cause buckling of the pad when debonding the bracket from the tooth.

7. The combination of a ceramic orthodontic bracket having a tooth-facing side and a relatively thin and flexible plastic pad, said pad having a bracket-attaching side adhesively secured to the tooth-facing side of the bracket, and a tooth-attaching side adapted to be bonded to the surface of a tooth, the tooth-facing side of the bracket and the bracket-attaching side of the pad including means for aligning the pad to the bracket when adhesively attaching the pad to the bracket, and said pad being sized to extend laterally beyond at least one edge of the tooth-engaging side of the bracket to be engageable by means for application of a compressive force to cause buckling of the pad when debonding the bracket from the tooth.

8. A method of debonding a ceramic bracket from a tooth which comprises, the steps of adhesively securing a relatively flexible plastic base/pad to the bracket prior to bonding to a tooth with a bonding adhesive, wherein the plastic base/pad is mesiodistally wider than the bracket and of a polycarbonate plastic, and applying and distorting force to the base/pad such as to cause it to distort and break the bond between the base/pad and the ceramic bracket.

* * * * *

UNITED STATES PATENT AND TRADEMARK OFFICE
CERTIFICATE OF CORRECTION

PATENT NO. : 5,098,288
DATED : March 24, 1992
INVENTOR(S) : Peter C. Kesling

It is certified that error appears in the above-identified patent and that said Letters Patent is hereby corrected as shown below:

```
Col. 4, line 21, change "31" to --21--;
        line 22, change "21" to --20--;
        line 35, change "31" to --21--;
Col. 6, line 36, change "curvature" to --curvate--;
Col. 7, line 15, change "ate" to --mate--;
        line 28, change "interferers" to --interferes--;
        line 40, change "problems" to --problem--;
Col. 8, line 23, change "he" to --the--; and
        line 58, change "and" to --a--.
```

Signed and Sealed this

Eighth Day of June, 1993

Attest:

MICHAEL K. KIRK

Attesting Officer

Acting Commissioner of Patents and Trademarks